United States Patent
Langhals et al.

Patent Number: 5,929,239
Date of Patent: *Jul. 27, 1999

[54] BIFLUOROPHORIC PERYLENE COLOURANTS

[75] Inventors: Heinz Langhals, Ottobrunn; Josef Gold, Pfaffenhofen, both of Germany

[73] Assignee: Ciba Specialty Chemicals Corporation, Tarrytown, N.Y.

[*] Notice: This patent is subject to a terminal disclaimer.

[21] Appl. No.: 09/013,658

[22] Filed: Jan. 26, 1998

[30] Foreign Application Priority Data

Jan. 27, 1997 [DE] Germany ............ 197 02 826

[51] Int. Cl.⁶ .............. C07D 221/22; C07D 239/02
[52] U.S. Cl. .............. 546/37; 544/322
[58] Field of Search .............. 546/37; 544/322

[56] References Cited

U.S. PATENT DOCUMENTS 5,508,137  4/1996  Langhals .................. 430/78
5,693,808  12/1997 Langhals .................. 546/37

FOREIGN PATENT DOCUMENTS 4018830  12/1991  Germany.

OTHER PUBLICATIONS

Langhals et al., J. Prakt. Chem., 338, (1996), pp. 654–659.

Heterocycles, vol. 40, No. 1, 1995, pp. 477–500.

Liebigs Ann./Recueil, 1997, pp. 1151–1153.

Primary Examiner—Alan L. Rotman
Assistant Examiner—Charanjit S. Aulakh
Attorney, Agent, or Firm—David R. Crichton

[57] ABSTRACT

Perylene-3,4:9,10-tetracarboxylic acid imides of the general formula I, including their optical antipodes and their mixtures, in particular their racemates

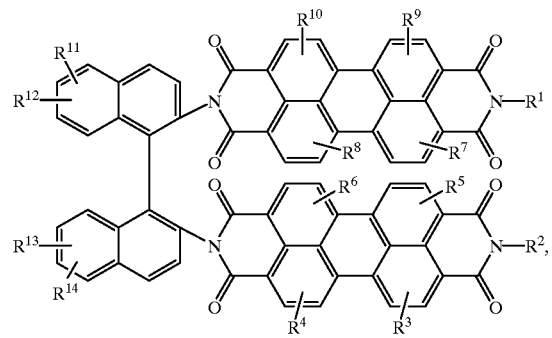

wherein $R^1$ to $R^{14}$ are identical or different and are hydrogen or a radical selected from the group consisting of an unsubstituted or substituted carbocyclic aromatic radical, an unsubstituted or substituted heterocyclic aromatic radical, halogen, unsubstituted or substituted $C_1$–$C_{18}$alkyl, —$OR^{15}$, —CN, —$NR^{16}R^{17}$, —$COR^{18}$, —$NR^{19}COR^{18}$, —$NR^{15}COOR^{18}$, —$NR^{15}CONR^{16}R^{17}$, —$NHSO_2R^{18}$, —$SO_2R^{18}$, —$SOR^{18}$, —$SO_2OR^{18}$, —$CONR^{16}R^{17}$—$N=NR^{20}$, —$OCOR^{18}$ and —$OCONHR^{18}$, where pairs of adjacent radicals can form a carbocyclic or heterocyclic ring, wherein $R^{18}$ is $C_1$14 $C_{18}$alkyl, $C_6$–$C_{10}$aryl, or benzyl which is unsubstituted or substituted by halogen, $C_1$–$C_4$alkyl or $C_1$–$C_4$alkoxy, or a 5- to 7-membered heterocyclic radical, $R^{16}$ and $R^{17}$ are each independently of the other hydrogen; $C_1$–$C_{18}$alkyl, $C_3$- to $C_{24}$cycloalkyl, $C_6$–$C_{10}$aryl or 5- to 7-membered heteroaryl, each of which is unsubstituted or substituted by cyano groups or hydroxyl groups, or wherein $R^{16}$ and $R^{17}$, together with at least one of the other radicals $R^1$ to $R^{14}$, are a 5- or 6-membered carbocyclic or heterocyclic ring, $R^{15}$ is hydrogen, $C_1$–$C_{18}$alkyl, $C_3$- to $C_{24}$cycloalkyl, $C_6$–$C_{10}$aryl or 5- to 7-membered heteroaryl, $R^{19}$ is hydrogen; $C_1$–$C_{18}$alkyl, $C_3$- to $C_{24}$cycloalkyl, $C_1$–$C_4$alkylaryl, each of which is unsubstituted or substituted by cyano groups, hydroxyl groups or $C_1$–$C_4$alkoxycarbonyl groups; $C_6$–$C_{10}$-aryl which is unsubstituted or substituted by halogen, $C_1$–$C_4$alkyl groups or by $C_1$–$C_4$alkoxy groups, or a 5- to 7-membered heterocycle, and $R^{20}$ is the radical of a coupling component, or $C_6$–$C_{10}$aryl which is unsubstituted or substituted by halogen, $C_1$–$C_4$alkyl groups or by $C_1$–$C_4$alkoxy groups, as well as a process for their preparation and use.

10 Claims, No Drawings

BIFLUOROPHORIC PERYLENE COLOURANTS

The present invention relates to perylene-3,4:9,10-tetracarboxylic acid imides of the general formula I, including their optical antipodes and their mixtures, in particular their racemates

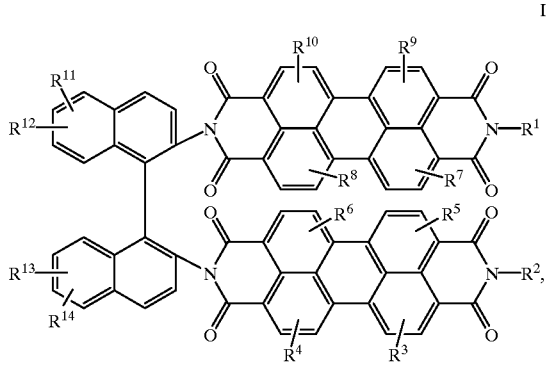

I wherein $R^1$ to $R^{14}$ are identical or different and are hydrogen or a radical selected from the group consisting of an unsubstituted or substituted carbocyclic aromatic radical, an unsubstituted or substituted heterocyclic aromatic radical, halogen, unsubstituted or substituted $C_1$–$C_{18}$alkyl, —$OR^{15}$, —CN, —$NR^{16}R^{17}$, —$COR^{18}$, —$NR^{19}COR^{18}$, —$NR^{15}COOR^{18}$, —$NR^{15}CONR^{16}R^{17}$, —$NHSO_2R^{18}$, —$SO_2R^{18}$, —$SOR^{18}$, —$SO_2OR^{18}$, —$CONR^{16}R^{17}$, —$SO_2NR^{16}R^{17}$, —$N=NR^{20}$, —$OCOR^{18}$ and —$OCONHR^{18}$, where pairs of adjacent radicals can form a carbocyclic or heterocyclic ring, wherein $R^{18}$ is $C_1$–$C_{18}$alkyl, $C_6$–$C_{10}$aryl, or benzyl which is unsubstituted or substituted by halogen, $C_1$–$C_4$alkyl or $C_1$–$C_4$alkoxy, or a 5- to 7-membered heterocyclic radical, $R^{16}$ and $R^{17}$ are each independently of the other hydrogen; $C_1$–$C_{18}$alkyl, $C_3$- to $C_{24}$ cycloalkyl, $C_6$–$C_{10}$aryl or 5- to 7-membered heteroaryl, each of which is unsubstituted or substituted by cyano groups or hydroxyl groups, or wherein $R^{16}$ and $R^{17}$, together with at least one of the other radicals $R^1$ to $R^{14}$, are a 5- or 6-membered carbocyclic or heterocyclic ring, $R^{15}$ is hydrogen, $C_1$–$C_{18}$alkyl, $C_3$- to $C_{24}$cycloalkyl, $C_6$–$C_{10}$aryl or 5- to 7-membered heteroaryl, $R^{19}$ is hydrogen; $C_1$–$C_{18}$alkyl, $C_3$- to $C_{24}$cycloalkyl, $C_1$–$C_4$alkylaryl, each of which is unsubstituted or substituted by cyano groups, hydroxyl groups or $C_1$–$C_4$alkoxycarbonyl groups; $C_6$–$C_{10}$-aryl which is unsubstituted or substituted by halogen, $C_1$–$C_4$alkyl groups or by $C_1$–$C_4$alkoxy groups, or a 5- to 7-membered heterocycle, and $R^{20}$ is the radical of a coupling component, or $C_6$–$C_{10}$aryl which is unsubstituted or substituted by halogen, $C_1$–$C_4$alkyl groups or by $C_1$–$C_4$alkoxy groups.

This invention also relates to a process for the preparation of the novel compounds I and to their use as colourants.

Perylene-3,4:9,10-tetracarboxylic acid bisimide ("perylene bisimides") have been valued for for a long time as lightfast textile dyes, pigments and fluorescent dyes (see, for example, Heterocycles 40 (1995) 477). The substituents at the imide atoms usually have only little influence on the UV/Vis spectra of the perylene bisimides. While this invariant spectral behaviour is usually desirable when the perylene bisimides are used in fluorescence marking, it is unsatisfactory for other other applications.

Perylene bisimides can be substituted at the phenyl rings ("ring-substituted") to influence the UV/Vis behaviour. However, this has the disadvantage that the chromophoric system and some of the substituents adversely affect product properties such as the photostability of the colourants.

Another possibility for changing the UV/Vis behaviour while maintaining the original chromophore consists in the selective interaction of several chromophores as it is known, for example, from the so-called aggregate formation. The disadvantage of perylene bisimide aggregate formation is the quenching, i.e. the at least partial quenching, of the desired fluorescence.

Accordingly, it is the object of this invention to provide perylene bisimide derivatives which do not have the above-mentioned disadvantages. In particular, perylene bisimides should be provided, the fluorescence of which is shifted towards the longwave as compared to the corresponding starting compounds. In addition, soluble perylene bisimides having the desired properties should also be provided.

Accordingly, the novel perylene-3,4:9,10-tetracarboxylic acid imides I have been found.

In addition, a process has been found for their preparation and use as colourants.

According to this invention, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ are identical or different and are hydrogen or a radical selected from the group consisting of an unsubstituted or substituted carbocyclic aromatic radical, an unsubstituted or substituted heterocyclic aromatic radical, halogen, unsubstituted or substituted $C_1$–$C_{18}$alkyl, —$OR^{15}$, —CN, —$NR^{16}R^{17}$, —$COR^{18}$, —$NR^{19}COR^{18}$, —$NR^{15}COOR^{18}$, —$NR^{15}CONR^{16}R^{17}$, —$NHSO_2R^{18}$, —$SO_2R^{18}$, —$SOR^{18}$, —$SO_2OR^{18}$, —$CONR^{16}R^{17}$, —$SO_2NR^{16}R^{17}$, —$N=NR^{20}$, —$OCOR^{18}$ and —$OCONHR^{18}$, where pairs of adjacent radicals can form a carbocyclic or heterocyclic ring, wherein $R^{18}$ is $C_1$–$C_{18}$alkyl, $C_6$–$C_{10}$aryl, or benzyl which is unsubstituted or substituted by halogen, $C_1$–$C_4$alkyl or $C_1$–$C_4$alkoxy, or a 5- to 7-membered heterocyclic radical, $R^{16}$ and $R^{17}$ are each independently of the other hydrogen; $C_1$–$C_{18}$alkyl, $C_3$- to $C_{24}$cycloalkyl, $C_6$–$C_{10}$aryl or 5- to 7-membered heteroaryl, each of which is unsubstituted or substituted by cyano groups or hydroxyl groups, or wherein $R^{16}$ and $R^{17}$, together with at least one of the other radicals $R^1$ to $R^{14}$, form a 5- or 6-membered carbocyclic or heterocyclic ring, $R^{15}$ is hydrogen, $C_1$–$C_{18}$alkyl, $C_3$- to $C_{24}$cycloalkyl, $C_6$–$C_{10}$aryl or 5- to 7-membered heteroaryl, $R^{19}$ is hydrogen; $C_1$–$C_{18}$alkyl, $C_3$- to $C_{24}$cycloalkyl, $C_1$–$C_4$alkylaryl, each of which is unsubstituted or substituted by cyano groups, hydroxyl groups or $C_1$–$C_4$alkoxycarbonyl groups; $C_6$–$C_{10}$-aryl which is unsubstituted or substituted by halogen, $C_1$–$C_4$alkyl groups or by $C_1$–$C_4$alkoxy groups, or a 5- to 7-membered heterocycle, and $R^{20}$ is the radical of a coupling component, or $C_6$–$C_{10}$aryl which is unsubstituted or substituted by halogen, $C_1$–$C_4$alkyl groups or by $C_1$–$C_4$alkoxy groups.

The unsubstituted or substituted carbocyclic aromatic radical may be preferably mono- to tetracyclic, particularly preferably mono- and bicyclic, radicals containing five to seven carbon atoms per ring, for example phenyl, diphenyl and naphthyl.

The unsubstituted or substituted heterocyclic aromatic radical may be preferably a mono- to tricyclic radical which preferably contains five to seven ring atoms. This radical may consist just of at least one heterocyclic ring or the heterocyclic ring or rings may contain at least one fused benzene ring. Examples to be mentioned are pyridyl, pyrimidyl, pyrazinyl, triazinyl, furanyl, pyrrolyl, thiophenyl, quinolyl, isoquinolyl, coumarinyl, benzofuranyl, benzimidazolyl, benzoxazolyl, dibenzofuranyl, benzothiophenyl, dibenzothiophenyl, indolyl, carbazdyl, pyrazolyl, imidazolyl, oxazolyl, isoxazolyl, thiazolyl, indazolyl, benzothiazolyl pyridazinyl, cinnolyl, quinazolyl, quinoxalyl, phthalazinyl, phthalazindionyl, phthalimidyl, chromonyl, naphtholactamyl, benzopyridonyl, ortho-sulfobenzimidyl, maleinimidyl, naphtharidinyl, benzimidazolonyl, benzoxazolonyl, benzothiazolonyl, benzothiazolonyl, quinazolonyl, pyrimidyl, quinoxalonyl, phthalazonyl, dioxapyrinidinyl, pyridonyl, isoquinolonyl, isothiazolyl, benzisoxazolyl, benzisothiazolyl, indazolonyl, acridinyl, acridonyl, quinazolindionyl, benzoxazindionyl, benzoxazinonyl and phthalimidyl.

In a preferred embodiment of this invention, the carbocyclic and/or heterocyclic aromatic radicals are mono- or polysubstituted by customary substituents, particularly preferably by substituents which do not bring about water-solubility. Examples to be mentioned are:

halogen, typically fluoro, chloro, bromo and iodo, preferably chloro;

the cyano group —CN;

unsubstituted or substituted $C_1$–$C_{18}$alkyl, for example methyl, ethyl, n-propyl, isopropyl, n-butyl, i-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably $C_1$–$C_{12}$alkyl, such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, particularly preferably $C_1$–$C_8$alkyl, such as methyl, ethyl, n-propyl, isopropyl, n-butyl, i-butyl, sec-butyl, tert-butyl, tert-amyl, n-hexyl, 1,1,3,3,-tetramethylbutyl, n-heptyl, n-octyl, 3-pentyl, 4-heptyl, 3-hexyl, 3-heptyl, very particularly preferably $C_1$–$C_4$alkyl, such as methyl, ethyl, n-propyl, isopropyl, n-butyl, i-butyl, sec-butyl, tert-butyl;

where the cited alkyl groups can be substituted by the following groups which usually do not increase hydrophilicity, for example fluoro, cyano, —OCOR$^{18}$, —OR$^{16}$, —CON(R$^{16}$)(R$^{17}$) or —OCONHR$^{18}$, wherein R$^{18}$ is $C_1$–$C_{18}$alkyl, such as methyl, ethyl, n-propyl, isopropyl, n-butyl, i-butyl, sec-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably $C_1$–$C_{12}$alkyl, such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, $C_6$–$C_{10}$aryl, such as phenyl, 2,5-di-tert-butylphenyl and naphthyl, preferably phenyl, naphthyl, or benzyl which is unsubstituted or substituted by halogen, such as chloro and fluoro, preferably fluoro, $C_1$–$C_4$-alkyl or —O—$C_1$–$C_4$alkyl, or a 5- to 7-membered heterocyclic radical, such as pyridyl, pyrimidyl, pyrazinyl, triazinyl, furanyl, pyrrolyl, thiophenyl, quinolyl, isoquinolyl, coumarinyl, and R$^{16}$ and R$^{17}$ are hydrogen; $C_1$–$C_{18}$alkyl which is unsubstituted or cyano group- or hydroxyl group-substituted as mentioned above, preferably $C_1$–$C_{12}$alkyl, particularly preferably $C_1$–$C_8$alkyl, very particularly preferably $C_1$–$C_4$alkyl, as mentioned above, $C_3$- to $C_{24}$cycloalkyl, preferably $C_5$-, $C_6$-, $C_{12}$-, $C_{15}$-, $C_{16}$-, $C_{20}$- and $C_{24}$cycloalkyl, aryl or heteroaryl, preferably derived from the above-mentioned carbo- and heterocyclic aromatic radicals, in particular phenyl which is unsubstituted or substituted by halogen, $C_1$–$C_4$alkyl or $C_1$–$C_4$alkoxy, or wherein R$^{16}$ and R$^{17}$, together with at least one of the other radicals R$^1$ to R$^{14}$, form a 5- to 6-membered ring or also a hetero ring, for example a pyridine, pyrrole, furane or pyrane ring, preferred —OR$^{16}$ radicals being hydroxy, —O-methyl, —O-ethyl, —O-i-propyl-, —O-i-butyl, —O-phenyl, —O-2,5-di-tert-butylphenyl, preferred —CON(R$^{16}$)(R$^{17}$) radicals being –CONH$_2$, —CONMe$_2$, —CONEt$_2$, —CON(iPr)$_2$, —CON(iBu)$_2$, —CONPh$_2$, —CON(2,5-di-tert-butylphenyl)$_2$.

In another preferred embodiment of this invention, the substituents at the alkyl groups are mono- or dialkylated amino groups, aryl radicals, for example naphthyl or, preferably, phenyl which is unsubstituted or substituted by halogen, alkyl or —O-alkyl, or also heterocyclic aromatic radicals, such as 2-thienyl, 2-benzoxazolyl, 2-benzothiazolyl, 2-benzimidazolyl, 6-benzimidazolonyl, 2-, 3- or 4-pyridinyl, 2-, 4-, or 6-quinolyl or 1-, 3-4-, 6-, or 8-isoquinolyl radicals.

If the cited substituents in turn contain alkyl, then this alkyl can be branched or unbranched and preferably contains 1 to 18, in particular 1 to 12, more preferably 1 to 8 and, particularly preferably, 1 to 4, carbon atoms. Typical examples of unsubstituted alkyl groups are methyl, ethyl, n-propyl, isopropyl, n-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl; typical examples of substituted alkyl groups are hydroxymethyl, 2-hydroxyethyl, trifluoromethyl, trifluoroethyl, cyanomethyl, methoxycarbonylmethyl, acetoxymethyl or benzyl. —OR$^{15}$, wherein R$^{15}$ is hydrogen, $C_1$–$C_{18}$alkyl as defined for R$^{18}$, including the preferred variants cited there, $C_3$- to $C_{24}$cycloalkyl, preferably $C_5$-, $C_6$-, $C_{12}$-, $C_{15}$-, $C_{16}$-, $C_{20}$-and $C_{24}$cycloalkyl, $C_6$–$C_{16}$aryl, such as naphthyl and phenyl, preferably unsubstituted phenyl and phenyl which is substituted by halogen, $C_1$–$C_4$alkyl or $C_1$–$C_4$alkoxy, or 5- to 7-membered heteroaryl. Examples of preferred radicals R$^{15}$ to be mentioned are: methyl, ethyl, n-propyl, isopropyl, n-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m-, or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl and pyranylmethyl; preferred —OR$^{15}$ radicals are hydroxy, methoxy, —O-ethyl, —O-i-propyl-, —O-i-butyl, —O-phenyl, —O-2,5-di-tert-butylphenyl;

—NR$^{16}$R$^{17}$, wherein R$^{16}$ and R$^{17}$ have the meanings mentioned above. Examples of preferred radicals to be mentioned are: amino, methylamino, dimethylamino, ethylamino, diethylamino, isopropylamino, 2-hydroxyethylamino, 2-hydroxypropylamino, N,N-bis(2-hydroxyethyl)amino, cyclopentylamino, cyclohexylamino, cyclododecyl-amino, cyclopentadecylamino, cyclohexadecylamino, cycloeicosanylamino, cyclotetracosanylamino, phenylamino, N-methylphenylamino, benzylamino, dibenzylamino, piperidyl or morpholyl;

—COR$^{18}$, wherein R$^{18}$ has the meaning cited above. Examples of preferred radicals R$^{18}$ to be mentioned are: methyl, ethyl, n-propyl, isopropyl, n-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m-, or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl, pyranylmethyl and furfuryl;

—NR$^{19}$COR$^{18}$, wherein R$^{18}$ has the meaning given above, and R$^{19}$ is hydrogen; C$_1$–C$_{18}$alkyl, C$_3$- to C$_{24}$cycloalkyl, C$_1$–C$_4$alkylaryl, each of which is unsubstituted or substituted by cyano groups, hydroxyl groups or C$_1$–C$_4$alkoxycarbonyl groups; C$_6$–C$_{10}$aryl which is unsubstituted or substituted by halogen, C$_1$–C$_4$alkyl groups or by C$_1$–C$_4$alkoxy groups, or a 5- to 7-membered heterocycle, the meaning of the individual radicals, such as alkyl, alkoxy, aryl etc., conforming to the above definitions thereof, including the preferred ranges cited there. Examples of radicals to be mentioned are: acetylamino, propionylamino, butyrylamino, benzoylamino, p-chlorobenzoylamino, p-methylbenzoylamino, N-methylacetamino, N-methylbenzoylamino, N-succinimido, N-phthalimido or N-(4-amino)-phthalimido;

—NR$^{15}$COOR$^{18}$, wherein R$^{18}$ and R$^{15}$ have the meanings given above. Examples of radicals to be mentioned are: —NHCOOCH$_3$, —NHCOOC$_2$H$_5$ and —NHCOOC$_6$H$_5$;

—NR$^{15}$CONR$^{16}$R$^{17}$, wherein R$^{16}$, R$^{17}$ and R$^{15}$ have the meanings given above. Examples of radicals to be mentioned are: ureido, N-methylureido, N-phenylureido or N,N'-2',4'-di-methylphenylureido;

—NHSO$_2$R$^{18}$, wherein R$^{18}$ has the meaning given above. Examples of radicals to be mentioned are: methylsulfonylamino, phenylsulfonylamino, p-tolylsulfonylamino or 2-naphthylsulfonylamino;

—SO$_2$R$^{18}$, wherein R$^{18}$ has the meaning given above. Examples of radicals to be mentioned are: methylsulfonyl, ethylsulfonyl, phenylsulfonyl, 2-naphthylsulfonyl;

—SOR$^{18}$, wherein R$^{18}$ has the meaning cited above. A radical to be mentioned as example is phenylsulfoxidyl;

—SO$_2$OR$^{18}$, wherein R$^{18}$ has the meaning given above. Examples of R18 to be mentioned are: methyl, ethyl, phenyl, o-, m- or p-chlorophenyl, o-, m- or p-methylphenyl, 1- or 2-naphthyl;

—CONR$^{16}$R$^{17}$, wherein R$^{16}$ and R$^{17}$ have the meanings given above. Examples of radicals to be mentioned are: carbamoyl, N-methylcarbamoyl, N-ethylcarbamoyl, N-phenylcarbamoyl, N,N-dimethylcarbamoyl, N-methyl-N-phenylcarbamoyl, N-1-naphthylcarbamoyl or N-piperdylcarbamoyl;

—SO$_2$NR$^{16}$R$^{17}$, wherein R$^{16}$ and R$^{17}$ have the meanings cited above. Examples of radicals to be mentioned are: sulfamoyl, N-methylsulfamoyl, N-ethylsulfamoyl, N-phenylsulfamoyl, N-methyl-N-phenylsulfamoyl or N-morpholylsulfamoyl;

—N=NR$^{20}$, wherein R$^{20}$ is the radical of a coupling component or a phenyl radical which is unsubstituted or substituted by halogen, alkyl or —O-alkyl, where halogen and alkyl have the meanings given above. Alkyl in the definitions of R$^{20}$ can contain one of the preferred numbers of carbon atoms indicated above. Examples of R$^{20}$ to be mentioned are: the acetoacetarylide, pyrazolyl, pyridonyl, o-, p-hydroxyphenyl, o-hydroxynaphthyl, p-amino-phenyl or p-N,N-dimethylaminophenyl radicals.

—OCOR$^{18}$, wherein R$^{18}$ has the meaning cited above. Examples of R$^{18}$ to be mentioned are: methyl, ethyl, phenyl, o-, m- or p-chlorophenyl;

—OCONHR$^{18}$, wherein R$^{18}$ has the meaning cited above. Examples of R$^{18}$ to be mentioned are: methyl, ethyl, phenyl, o-, m- or p-chlorophenyl.

Halogen may be fluoro, chloro, bromo and iodo. Fluoro and chloro are preferred.

Unsubstituted or substituted C$_1$–C$_{18}$alkyl can be: methyl, ethyl, n-propyl, isopropyl, n-butyl, i-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably C$_1$–C$_{12}$alkyl, such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, particularly preferably C$_1$–C$_8$alkyl, such as methyl, ethyl, n-propyl, isopropyl, n-butyl, i-butyl, sec-butyl, tert-butyl, tert-amyl, n-hexyl, 1,1,3,3,-tetramethylbutyl, n-heptyl, n-octyl, 3-pentyl, 4-heptyl, 3-hexyl, 3-heptyl, very particularly preferably C$_1$–C$_4$alkyl, such as methyl, ethyl, n-propyl, isopropyl, n-butyl, i-butyl, sec-butyl, tert-butyl;

where the cited alkyl groups can be substituted with the following groups which usually do not increase the hydrophilicity, for example fluoro, hydroxy, cyano, —OCOR$^{18}$, —OR$^{16}$, —CON(R$^{16}$)(R$^{17}$) or —OCONHR$^{18}$, wherein R$^{18}$ is C$_1$–C$_{18}$alkyl, typically methyl, ethyl, n-propyl, isopropyl, n-butyl, i-butyl, sec-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably C$_1$–C$_{12}$alkyl, such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, C$_6$–C$_{10}$aryl, such as phenyl and naphthyl, preferably naphthyl, or benzyl which is unsubstituted or substituted by halogen, such as chloro and fluoro, preferably fluoro, C$_1$–C$_4$alkyl or —O—C$_1$–C$_4$alkyl, or a 5- to 7-membered heterocyclic radical, such as pyridyl, pyrimidyl, pyrazinyl, triazinyl, furanyl, pyrrolyl, thiophenyl, quinolyl, isoquinolyl, coumarinyl, and R$^{16}$ and R$^{17}$ are hydrogen; C$_1$–C$_{18}$alkyl which is unsubstituted or cyano group- or hydroxyl group-substituted as mentioned above, preferably C$_1$–C$_{12}$alkyl, particularly preferably C$_1$–C$_8$alkyl, very particularly preferably C$_1$–C$_4$alkyl as mentioned above, C$_3$-to C$_{24}$cycloalkyl, preferably C$_5$-, C$_6$-, C$_{12}$-, C$_{15}$-, C$_{16}$-, C$_{20}$- and C$_{24}$cycloalkyl, aryl or heteroaryl, preferably derived from the above-mentioned carbo- and heterocyclic aromatic radicals, in particular phenyl which is unsubstituted or substituted by halogen, C$_1$–C$_4$alkyl or C$_1$–C$_4$alkoxy, or wherein R$^{16}$ and R$^{17}$, together with at least one of the other radicals R$^1$ to R$^{14}$, form a 5- to 6-membered ring or also a hetero ring, for example a pyridine, pyrrole, furan or pyran ring.

In another preferred embodiment of this invention, the substituents at the alkyl groups are mono- or dialkylated amino groups, aryl radicals, such as naphthyl or, preferably, phenyl which is unsubstituted or substituted by halogen, alkyl or —O-alkyl, or also heterocyclic aromatic radicals, such as the 2-thienyl, 2-benzoxazolyl, 2-benzothiazolyl, 2-benzimidazolyl, 6-benzimidazolonyl, 2-, 3- or 4-pyridinyl, 2-, 4-, or 6-quinolyl or 1-, 3-, 4-, 6-, or 8-isoquinolyl radicals.

If the cited substituents in turn contain alkyl, then this alkyl can be branched or un-branched and preferably contains 1 to 18, in particular 1 to 12, more preferably 1 to 8 and, particularly preferably, 1 to 4, carbon atoms. Typical examples of unsubstituted alkyl groups are methyl, ethyl, n-propyl, isopropyl, n-butyl, sec-butyl, tertbutyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, and typical examples of substituted alkyl groups are hydroxymethyl, 2-hydroxyethyl, trifluoromethyl, trifluoroethyl, cyanomethyl, methoxycarbonylmethyl, acetoxymethyl or benzyl.

$R^{15}$ in —$OR^{15}$ can be: hydrogen, $C_1$–$C_{18}$alkyl as defined above for $R^{18}$, including the preferred variants mentioned there. Examples of preferred radicals $R^{15}$ to be mentioned are: methyl, ethyl, n-propyl, isopropyl, n-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m-, or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl and pyranylmethyl. Examples of preferred —$OR^{15}$ radicals are: hydroxy, methoxy, —O-ethyl, —O-i-propyl-, —O-i-butyl, —O-phenyl, —O-2,5-di-tert-butylphenyl.

$R^{16}$ and $R^{17}$ in —$NR^{16}R^{17}$ can be the radicals defined above. Typical examples of preferred radicals are: amino, methylamino, dimethylamino, ethylamino, diethylamino, isopropylamino, 2-hydroxyethylamino, 2-hydroxypropylamino, N,N-bis(2-hydroxyethyl)amino, cyclopentylamino, cyclohexylamino, cyclododecylamino, cyclopentadecylamino, cyclohecadecylamino, cycloeicosanylamino, cyclotetracosanylamino, phenylamino, N-methylphenylamino, benzylamino, dibenzylamino, piperidyl or morpholyl and, particularly preferably, dimethylamino, diethylamino, di-n-propylamino, di-n-butylamino, di-n-pentylamino, di-n-hexylamino, di-n-heptylamino, di-n-octylamino, di-n-dodecylamino.

$R^{16}$ and $R^{17}$ on their own or together with at least one of the other free radicals selected from $^1 R^2$, $R^3$, $R^4$, $R^5$, $R^6$, $R^7$, $R^8$, $R^9$, $R^{10}$, $R^{11}$, $R^{12}$, $R^{13}$ and $R^{14}$ can form one or several 5- or 6-membered saturated or unsaturated rings, typically pyridine, pyrrole, piperidine, quinoline or benzoquinolizine derivatives.

Suitable —$COR^{18}$ radicals can be those, wherein $R^{18}$ has the meaning given above. Examples of preferred radicals $R^{18}$ to be mentioned are: methyl, ethyl, n-propyl, isopropyl, n-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m-, or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl, pyranylmethyl and furfuryl.

—$NR^{19}COR^{18}$ radicals can be those, wherein $R^{18}$ has the meaning given above and $R^{19}$ is hydrogen; $C_1$–$C_{18}$alkyl, $C_3$- to $C_{24}$cycloalkyl, $C_1$–$C_4$alkylaryl, each of which is unsubstituted or substituted by cyano groups, hydroxyl groups or $C_1$–$C_4$alkoxycarbonyl groups; $C_6$–$C_{10}$aryl which is unsubstituted or substituted by halogen, $C_1$–$C_4$alkyl groups or by $C_1$–$C_4$alkoxy groups, or a 5- to 7-membered heterocycle, the meaning of the individual radicals, such as alkyl, alkoxy, aryl etc., conforming to the above definitions thereof, including the preferred ranges cited there, for example o-, m- or p-chlorophenyl, o-, m- or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienly, pyranylmethyl, benzyl or furfuryl. Examples of radicals to be mentioned are: acetylamino, propionylamino, butyrylamino, benzoylamino, p-chlorobenzoylamino, p-methylbenzoylamino, N-methylacetamino, N-methylbenzoylamino, N-succinimido, N-phthalimido or N-(4-amino)phthalimido.

—$NR^{15}COOR^{18}$ radicals can be those, wherein $R^{18}$ and $R^{15}$ have the meanings cited above. Examples to be mentioned are: —$NHCOOCH_3$, —$NHCOOC_2H_5$ and —$NHCOOC_6H_5$.

—$NR^{15}CONR^{16}R^{17}$ radicals can be those, wherein $R^{16}$, $R^{17}$ and $R^{15}$ have the meanings given above. Examples of radicals to be mentioned are: ureido, N-methylureido, N-phenylureido or N,N'-2', 4'-dimethylphenylureido.

—$NHSO_2R^{18}$ radicals can be those, wherein $R^{18}$ has the meaning given above. Examples of radicals to be mentioned are: methylsulfonylamino, phenylsulfonylamino, p-tolylsulfonylamino or 2-naphthylsulfonylamino.

—$SO_2R^{18}$ radicals can be those, wherein $R^{18}$ has the meaning given above. Examples of radicals to be mentioned are: methylsulfonyl, ethylsulfonyl, phenylsulfonyl, 2-naphthylsulfonyl.

—$SOR^{18}$ radicals can be those, wherein $R^{18}$ has the meaning given above. A radical to be mentioned as example is phenylsulfoxidyl.

—$SO_2OR^{18}$ radicals can be those, wherein $R^{18}$ has the meaning given above. Examples of $R^{18}$ are: methyl, ethyl, phenyl, o-, m- or p-chlorophenyl, o-, m- or p-methylphenyl, 1- or 2-naphthyl.

—$CONR^{16}R^{17}$ radicals can be those, wherein $R^{16}$ and $R^{17}$ have the meanings cited above. Examples of radicals to be mentioned are: carbamoyl, N-methylcarbamoyl, N-ethylcarbamoyl, N-phenylcarbamoyl, N,N-dimethylcarbamoyl, N-methyl-N-phenylcarbamoyl, N-1-naphthylcarbamoyl or N-piperidylcarbamoyl.

—$SO_2NR^{16}R^{17}$ radicals can be those, wherein $R^{16}$ and $R^{17}$ have the meanings given above. Examples of radicals to be mentioned are: sulfamoyl, N-methylsulfamoyl, N-ethylsulfamoyl, N-phenylsulfamoyl, N-methyl-N-phenylsulfamoyl or N-morpholylsulfamoyl.

—$N=NR^{20}$ radicals can be those, wherein $R^{20}$ is the radical of a coupling component or a phenyl radical which is unsubstituted or substituted by halogen, alkyl or —O-alkyl, wherein halogen and alkyl have the meanings given above. Alkyl in the definitions of $R^{20}$ can contain one of the preferred numbers of carbon atoms indicated above. Examples of $R^{20}$ to be mentioned are: the acetoacetarylide, pyrazolyl, pyridonyl, o-, p-hydroxyphenyl, o-hydroxynaphthyl, p-aminophenyl or p-N,N-dimethylaminophenyl radicals.

—OCOR$^{18}$ radicals can be those, wherein R$^{18}$ has the meaning cited above. Examples of radicals R$^{18}$ to be mentioned are: methyl, ethyl, phenyl, o-, m- or p-chlorophenyl.

—OCONHR$^{18}$ radicals can be those, wherein R$^{18}$ has the meaning cited above. Examples of R$^{18}$ to be mentioned are: methyl, ethyl, phenyl, o-, m- or p-chlorophenyl.

Particularly preferred perylene bisimides I are those, wherein R$^3$, R$^4$, R$^5$, R$^6$, R$^7$, R$^8$, R$^9$, R$^{10}$, R$^{11}$, R$^{12}$, R$^{13}$ and R$^{14}$ are hydrogen, and R$^1$ and R$^2$ are a secondary alkyl radical, such as 1-(C$_1$–C$_9$alkyl)—C$_2$–C$_{10}$alkyl, in particular those, wherein R$^1$ has a "swallowtail structure", for example 1-methylethyl, 1-ethyl-n-propyl, 1-n-propyl-n-butyl, 1-n-butyl-n-pentyl, 1-n-hexyl-1-heptyl, 1-n-heptyl-1-n-octyl, 1-n-octyl-1-n-nonyl, 1-n-nonyl-1-decyl, and also aromatic radicals, preferably phenyl radicals, very particularly preferably C$_1$–C$_6$alkyl-substituted phenyl such as 2,6-di-tert-butylphenyl and 2,5-di-tert-butylphenyl, or wherein R$^1$ and R$^2$ are C$_1$–C$_8$-alkyl, such as methyl, ethyl, n-propyl, isopropyl, n-butyl, i-butyl, sec-butyl, tert-butyl, tertamyl, n-hexyl, 1,1,3,3,-tetramethylbutyl, n-heptyl, n-octyl, 3-pentyl, 4-heptyl, 3-hexyl or 3-heptyl.

Those compounds wherein R$^1$ and/or R$^2$ =1-n-butyl-n-pentyl, 1-n-hexyl-1-heptyl, 1-n-heptyl-1-n-octyl, 1-n-octyl-1-n-nonyl, 1-n-nonyl-1-decyl and 2,5-di-tert-butylphenyl are particularly distinguished by their good solubility.

The novel perylene bisimides I are preferably obtained by reacting a perylene anhydride imide with a primary amine at elevated temperature in the presence of a catalyst and a base, by reacting a perylene-3,4:9,10-tetracarboxylic acid-3,4-anhydride-9,10-imide II

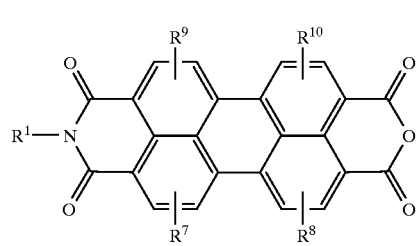

or a mixture of perylene anhydride imide II and perylene anhydride imide IIa

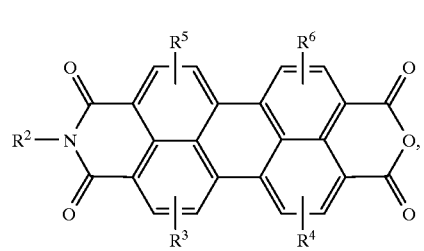

wherein R$^1$ to R$^1$ have the meanings cited above, with diaminonaphthalene III

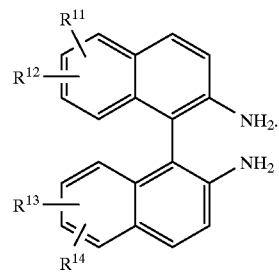

Perylene anhydride imides II and IIa are known and can be prepared by known methods, for example from the corresponding bisimides. Some compounds are described, inter alia, in Heterocycles 40 (1995) 477 and Chem.Ber. 118 (1985) 4641–4645.

Diaminonaphthalenes III, which are usually chiral, are also known from the literature and/or are commercially available. It is possible to use pure enantiomers (more precisely: atropisomers) or a mixture of enantiomers, e.g. a racemate.

The molar ratio of perylene anhydride imide II (or II+IIa) to diaminonaphthalene III is usually chosen in the range from 3:1 to 2.5:1, preferably from 2.1:1 to 1.9:1, more preferably from 2:1.

According to this invention, the reaction is carried out at elevated temperature, preferably in the range from 50 to 350° C., particularly preferably from 150 to 350° C., very particularly preferably from 150 to 200° C.

According to findings to date, the success of the reaction does not depend on the choice of the pressure range. For the sake of simplicity, the reaction is usually carried out at atmospheric pressure, but it is also possible to choose lower pressure ranges of up to 10 kPa or of up to 10 MPa.

The reaction times are preferably chosen in the range from 1 h to 10 h, depending on the chosen reaction temperature and on the educt.

Furthermore, the reaction is carried out in the presence of a base, preferably of a basic organic solvent, particularly preferably of a nitrogen-containing heterocycle such as imidazole, quinoline, pyridine, picoline or N-methylpyrrolidone, very particularly preferably imidazole.

The amount of base is usually chosen in the range from 0.1 to 1 mol per 1 kg/base, preferably from 0.1 to 0.5 mol per kg/base (perylene anhydride imide II (or II+IIa)/base).

The reaction is also carried out in the presence of a catalyst. Suitable catalysts are the zinc, lead, calcium, copper, manganese, iron, cobalt, nickel, tin, silver or magnesium salts, for example the chlorides, sulfates, nitrates and acetates thereof, preferably zinc acetate, zinc propionate, zinc chloride, lead acetate, calcium acetate, manganese acetate, cadmium acetate, iron(II)acetate and iron(III) acetate, cobalt acetate, copper acetate, nickel acetate, tin acetate, silver acetate or magnesium acetate, more preferably zinc acetate, lead acetate, zinc chloride, particularly preferably zinc acetate, also e.g. in the corresponding customary dihydrate form.

Usually, the molar ratio of perylene anhydride imide II (or II+IIa) to catalyst is in the range from 1:0.1 to 1:10, preferably from 1:0.5 to 1:5.

In a preferred embodiment of this invention, the reaction is carried out under a protective gas atmosphere. Suitable protective gases are typically nitrogen and the noble gases such as helium or argon.

The reaction mixture can be processed in per se customary manner, preferably by chromatography.

The novel perylene bisimides I are suitable for use as colourants, in particular as pigments and dyes, in general by methods known per se, preferably (a) for mass colouring polymers, where the polymers can be polyvinyl chloride, cellulose acetate, polycarbonates, polyamides, polyurethanes, polyimides, polybenzimidazoles, melamine resins, silicones, polyesters, polyethers, polystyrene, polymethyl methacrylate, polyethylene, polypropylene, polyvinyl acetate, polyacrylonitrile, polybutadiene, polychlorobutadiene or polyisoprene, or the copolymers of the cited monomers;

(b) as vat dyes or mordant dyes, for example for dyeing natural substances and, in particular, paper, wood, straw, leather, hides or natural fibre materials, such as cotton, wool, silk, jute, sisal, hemp, flax or animal hair (e.g. horsehair) and the conversion products thereof, such as viscose fibre, nitrate silk or cuprammonium rayon (rayon), preferred salts for mordanting being aluminium salts, chromium salts and iron salts;

(c) for the preparation of paints, paint systems, in particular automotive lacquers, coating compositions, paper colours, printing colours, inks, in particular for use in ink-jet printers, preferably in homogeneous solution as a fluorescent ink, and for painting and writing purposes, as well as in electrophotography, e.g. for dry copier systems (Xerox process) and laser printers;

(d) for security marking purposes, such as for cheques, cheque cards, currency notes, coupons, documents, identity papers and the like, where a special unmistakable colour impression is to be achieved;

(e) as an additive to colourants, such as pigments and dyes, where a specific colour shade is to be achieved, particularly in the case, where luminous shades are preferred;

(f) for marking objects for machine recognition of these objects via the fluorescence, preferably for machine recognition of objects for sorting, e.g. including the recycling of plastics, alphanumerical prints or barcodes being preferably used;

(g) for converting the frequency of light, e.g. for turning short-wave light into long-wave visible light or for doubling or tripling the frequency of laser light in non-linear optics;

(h) for the production of passive display elements for a multitude of display, notice and marking purposes, e.g. passive display elements, notices and traffic signs, such as traffic lights;

(i) as starting material for supraconducting organic materials (via π-π-interaction, the addition of e.g. iodine usually resulting in a intermediary charge delocalisation);

(j) for marking with fluorescence in the solid state;

(k) for decorative and artistic purposes;

(l) for tracer purposes, e.g. in biochemistry, medicine, technology and natural science, where the novel colourants can be linked covalently to the substrates or via secondary valences, such as hydrogen bonds or hydrophobic interactions (adsorption);

(m) as fluorescent dyes in highly sensitive detection processes (see C. Aubert, J. Fünfschilling, 1. Zschokke-Granacher and H. Langhals, Z. Analyt. Chem. 1985, 320, 361), in particular as fluorescent dyes in scintillators;

(n) as dyes or fluorescent dyes in optical light collection systems, in fluorescence solar collectors (see H. Langhals, Nachr. Chem. Tech. Lab. 1980, 28, 716), in fluorescence-activated displays (see W. Greubel and G. Baur, Elektronik 1977, 26, 6), in cold light sources used for light-induced polymerisation for the preparation of plastics, for testing of materials, for example in the production of semiconductor circuits, for analysing microstructures of integrated semiconductor components, in photoconductors, in photographic processes, in display, illumination or image converter systems, where excitation is effected by electrons, ions or UV radiation, e.g. in fluorescent displays, Braun tubes or in fluorescent lamps, as part of an integrated semiconductor circuit containing dyes as such or in combination with other semiconductors, for example in the form of an epitaxy, in chemiluminescence systems, e.g. in chemiluminescent flashlights, in luminescene immunoassays or other luminescence detection process, as signal paints, preferably for visually emphasising strokes of writing and drawings or other graphic products, for marking signs and other objects for which a particular visual colour impression is to be achieved, in dye lasers, preferably as fluorescent dyes for generating laser beams, in optical recording media, in color filters and also as Q-switches;

(o) and as rheology improvers.

The novel perylene bisimides I are additional very highly fluorescent perylene derivatives.

EXAMPLES

Example 1

(M)-(+)-2,2'-bisamino-1,1'-binaphthalene (250 mg, 0.879 mmol), N-(1-hexyl-heptyl)perylene-3,4:9,10-tetracarboxylic acid-3,4-anhydride-9,10-imide (1.06 g, 1.76 mmol) and 5.5 g of 1,3-imidazole are heated in the presence of 350 mg of zinc acetate and under argon for 4 hours to 170° C. After cooling this mixture, it is charged with 5 ml of water and 80 ml of ethanol and is then stood for at least 4 h. The precipitated solid is collected by suction via a D 4 glass frit and washed with ethanol. The product is chromatographed in chloroform over silica gel. Yield: 530 mg (42%), m.p.>350° C., $R_f$ (CHCl$_3$, silica gel)=0.37.

CD (CHCl$_3$): $\lambda_{max}$, $\lambda_{min}(\Delta\epsilon)$=533.9 nm (488.4), 519.0 (−128.5), 498.2 (76.2), 484.6 (−185.5), 466.0 (−32.6), 454.5 (−61.0). UV (CHCl$_3$): $\lambda_{max(\epsilon)}$=435 nm (12300), 461 (40600), 492 (108700), 529 sh, 535 (144400). Flourescence (CHCl$_3$): $\lambda_{max}$=543 nm, 583. Fluorescence in the solid state: $\lambda_{max}$=675 nm.

C$_{98}$H$_{90}$N$_4$O$_8$ (1451.8 g/mol): calcd.: C 81.08, H 6.25, N 3.86; found: C 81.06, H 6.29, N 3.75.

Example 2

The procedure of Example 1 is repeated, but replacing the (M)-(+)-atropisomer with the corresponding (P)-(−)-2,2'-bisamino-1,1'-binaphthalene.

Yield: 550 mg (43%), m.p.>350° C., $R_f$ (CHCl$_3$, silica gel)=0.37.

CD (CHCl$_3$): $\lambda_{max}$, $\lambda_{min}(\Delta\epsilon)$=534.2 nm (−484.8), 519.3 (122.4), 498.6 (−78.1), 484.9 (182.1) 466.5 (32.4), 455.0 (61.5). UV (CHCl$_3$): $\lambda_{max(\epsilon)}$=435 nm (12300), 461 (40600), 492 (108700), 529 sh, 535 (144400). Flourescence (CHCl$_3$): $\lambda_{max}$=543 nm, 583. Fluorescence in the solid state: $\lambda_{max}$=675 nm.

C$_{98}$H$_{90}$N$_4$O$_8$ (1451.8 g/mol): calcd.: C 81.08, H 6.25, N 3.86; found: C 81.34, H 6.31, N 3.97.

What is claimed is:

1. Perylene-3,4:9,10-tetracarboxylic acid imides of the general formula I, including their optical antipodes and their mixtures, in particular their racemates

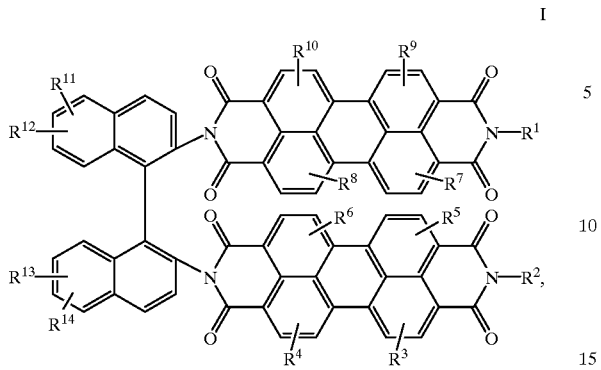

I wherein $R^1$ to $R^{14}$ are identical or different and are hydrogen or a radical selected from the group consisting of an unsubstituted or substituted carbocyclic aromatic radical, an unsubstituted or substituted heterocyclic aromatic radical, halogen, unsubstituted or substituted $C_1$–$C_{18}$alkyl, —$OR^{15}$, —CN, —$NR^{16}R^{17}$, —$COR^{18}$, —$NR^{19}COR^{18}$, —$NR^{15}COOR^{18}$, —$NR^{15}CONR^{16}R^{17}$, —$NHSO_2R^{18}$, —$SO_2R^{18}$, —$SOR^{18}$, —$SO_2OR^{18}$, —$CONR^{16}R^{17}$, —$SO_2NR^{16}R^{17}$, —N=$NR^{20}$, —$OCOR^{18}$ and —$OCONHR^{18}$, where pairs of adjacent radicals can form a carbocyclic or heterocyclic ring, wherein $R^{18}$ is $C_1$–$C_{18}$alkyl, $C_6$–$C_{10}$aryl, or benzyl which is unsubstituted or substituted by halogen, $C_1$–$C_4$alkyl or $C_1$–$C_4$alkoxy, or a 5- to 7-membered heterocyclic radical, $R^{16}$ and $R^{17}$ are each independently of the other hydrogen; $C_1$–$C_{18}$alkyl, $C_3$- to $C_{24}$cycloalkyl, $C_6$–$C_{10}$aryl or 5- to 7-membered heteroaryl, each of which is unsubstituted or substituted by cyano groups or hydroxyl groups, or wherein $R^{16}$ and $R^{17}$, together with at least one of the other radicals $R^1$ to $R^{14}$, are a 5- or 6-membered carbocyclic or heterocyclic ring, $R^{15}$ is hydrogen, $C_1$–$C_{18}$alkyl, $C_3$- to $C_{24}$cycloalkyl, $C_6$–$C_{10}$aryl or 5- to 7-membered heteroaryl, $R^{19}$ is hydrogen; $C_1$–$C_{18}$alkyl, $C_3$- to $C_{24}$cycloalkyl, $C_1$–$C_4$alkylaryl, each of which is unsubstituted or substituted by cyano groups, hydroxyl groups or $C_1$–$C_4$alkoxycarbonyl groups; $C_6$–$C_{10}$-aryl which is unsubstituted or substituted by halogen, $C_1$–$C_4$alkyl groups or by $C_1$–$C_4$alkoxy groups, or a 5- to 7-membered heterocycle, and $R^{20}$ is the radical of a coupling component, or $C_6$–$C_{10}$aryl which is unsubstituted or substituted by halogen, $C_1$–$C_4$alkyl groups or by $C_1$–$C_4$alkoxy groups.

2. A perylene-3,4:9,10-tetracarboxylic acid imide I according to claim 1, wherein $R^3$, $R^4$, $R^5$, $R^6$, $R^7$, $R^8$, $R^9$, $R^{10}$, $R^{11}$, $R^{12}$, $R^{13}$ and $R^{14}$ are hydrogen, $R^1$ and $R^2$ are a secondary alkyl radical, in particular 1-($C_1$–$C_9$alkyl)—$C_2$–$C_{10}$alkyl, or $R^1$ and $R^2$ are $C_1$–$C_8$alkyl.

3. A process for the preparation of the perylene-3,4:9,10-tetracarboxylic acid imides I according to claim 1 by reacting a perylene anhydride imide with a primary amine at elevated temperature in the presence of a catalyst and a base, which comprises reacting a perylene-3,4:9,10-tetracarboxylic acid-3,4-anhydride-9,10-imide II

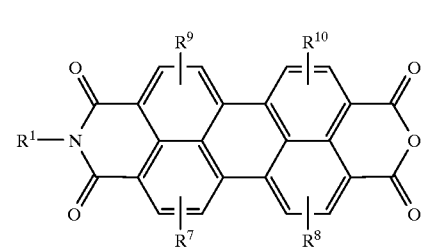

II or a mixture of perylene anhydride imide II and perylene anhydride imide IIa

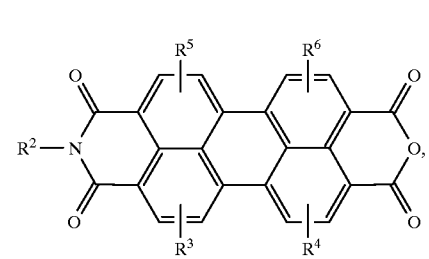

IIa wherein $R^1$ to $R^{10}$ have the meanings cited above, with diaminonaphthalene III

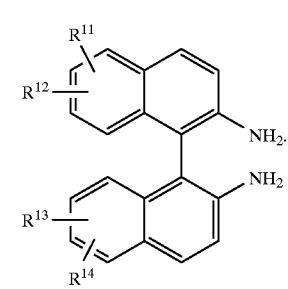

III

4. A process according to claim 3, wherein the molar ratio of perylene anhydride imide II (or II+IIa) to diaminonaphthalene III is in the range from 3:1 to 2.5:1.

5. A process according to claim 3, which comprises carrying out the reaction in the temperature range from 50 to 350° C.

6. A process according to claim 4, which comprises carrying out the reaction in the temperature range from 50 to 350° C.

7. A process according to claim 3, which comprises carrying out the reaction in the presence of a basic organic solvent.

8. A process according to claim 7, wherein the amount of basic organic solvent is in the range from 0.1 to 1 mol per 1 kg/base, preferably from 0.1 to 0.5 mol per kg/base (perylene anhydride imide II (or II+IIa)/base).

9. A process according to claim 3, which comprises carrying out the reaction in the presence of a zinc, lead, calcium, copper, manganese, iron, cobalt, nickel, tin, silver or magnesium salt, in particular of the chlorides, sulfates, nitrates or acetates thereof.

10. A process according to claim 8, which comprises carrying out the reaction in the presence of a zinc, lead, calcium, copper, manganese, iron, cobalt, nickel, tin, silver or magnesium salt, in particular of the chlorides, sulfates, nitrates or acetates thereof.

* * * * *